(12) United States Patent
Rowe et al.

(10) Patent No.: US 9,513,180 B2
(45) Date of Patent: Dec. 6, 2016

(54) SLIDING PISTON PRESSURE INDICATOR

(71) Applicant: TELEFLEX MEDICAL INCORPORATED, Research Triangle Park, NC (US)

(72) Inventors: David Troy Rowe, Sinking Spring, PA (US); John C. Victor, Kunkletown, PA (US); Jeffrey Vitullo, Pottstown, PA (US); Rodney Wilmer Denlinger, Lancaster, PA (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 279 days.

(21) Appl. No.: 14/209,558

(22) Filed: Mar. 13, 2014

(65) Prior Publication Data
US 2014/0260962 A1    Sep. 18, 2014

Related U.S. Application Data

(60) Provisional application No. 61/784,772, filed on Mar. 14, 2013, provisional application No. 61/813,072, filed on Apr. 17, 2013.

(51) Int. Cl.
*A61M 16/04* (2006.01)
*G01L 7/16* (2006.01)

(52) U.S. Cl.
CPC ............ *G01L 7/163* (2013.01); *A61M 16/044* (2013.01)

(58) Field of Classification Search
CPC .............................. A61M 16/044; G01L 7/163
USPC .................. 91/1; 92/5 R; 604/97.03; 73/1.68
See application file for complete search history.

(56) References Cited

U.S. PATENT DOCUMENTS

| 4,526,196 A * | 7/1985 | Pistillo ................ A61M 16/044 128/207.15 |
| 4,583,917 A | 4/1986 | Shah |
| 4,727,887 A | 3/1988 | Haber |
| 5,336,183 A * | 8/1994 | Greelis ............. A61M 25/1018 604/100.01 |
| 8,277,399 B2 | 10/2012 | Hamilton et al. |
| 8,291,768 B2 | 10/2012 | Spiegel et al. |
| 2006/0231013 A1* | 10/2006 | Lane ....................... G01L 7/166 116/272 |

(Continued)

FOREIGN PATENT DOCUMENTS

| CN | 102281913 A | 12/2011 |
| EP | 2319408 A1 | 5/2011 |

(Continued)

*Primary Examiner* — Thomas E Lazo
(74) *Attorney, Agent, or Firm* — Baker & Hostetler LLP

(57) ABSTRACT

A fluid pressure indicating device is disclosed. The pressure indicating device includes a housing defining a cylindrical bore therein, and a piston movably disposed within the cylindrical bore. The housing includes a first portion that is permeable to visible light, a first end member, and a second end member opposite the first end member. A first variable volume is defined by the cylindrical bore, the piston, and the first end member of the housing. An inlet port is defined by the first end member of the housing and is in fluid communication with the first variable volume. A piston bypass channel is disposed outside the cylindrical bore and is in fluid communication with the inlet port. An outlet port is defined by the second end member, such that the outlet port is in fluid communication with the piston bypass channel.

18 Claims, 5 Drawing Sheets

(56) References Cited

U.S. PATENT DOCUMENTS

| | | | |
|---|---|---|---|
| 2010/0179488 A1 | 7/2010 | Spiegel et al. | |
| 2010/0326442 A1 | 12/2010 | Hamilton et al. | |
| 2011/0220118 A1* | 9/2011 | Lowenstein | A61M 16/044 |
| | | | 128/207.15 |
| 2012/0245471 A1* | 9/2012 | Langewouters | A61B 5/02255 |
| | | | 600/473 |

FOREIGN PATENT DOCUMENTS

| | | |
|---|---|---|
| JP | 2004219335 | 8/2004 |
| JP | 2013507210 | 3/2013 |
| WO | 2011045138 A1 | 4/2011 |

* cited by examiner

SLIDING PISTON PRESSURE INDICATOR

CROSS REFERENCE TO RELATED APPLICATION

This application claims the benefit of U.S. Provisional Application No. 61/784,772, filed on Mar. 14, 2013, and of U.S. Provisional Application No. 61/813,072, filed on Apr. 17, 2013, the disclosures of which are hereby incorporated by reference in their entireties.

FIELD OF THE INVENTION

The present invention relates generally to pressure indicators. More particularly, the present invention relates to a pressure indicator suitable for an inflatable cuff of an endotracheal tube.

BACKGROUND OF THE INVENTION

Inflatable cuffs have been proposed for applying occlusive pressure to a flow lumen of a patient's body, or for sealing between a medical instrument and a flow lumen of a patient's body. For example, an endotracheal tube may include an inflatable cuff that conforms to the contours of a patient's trachea when inserted into the trachea and inflated to seal a gap between the endotracheal tube and the trachea. Further, pressure indicators have been proposed for monitoring a fluid pressure within an inflatable cuff.

U.S. Pat. No. 4,727,887 (hereinafter "the '887 patent") describes an artificial sphincter with an occlusion cuff for applying occlusive pressure to a flow lumen of a patient's body (e.g., a urethra). The '887 patent further proposes a combination hypodermic manometer including a piston assembly which is adapted for reciprocal movement through a fluid-filled sleeve. As the piston assembly of the '887 patent is moved through the sleeve, a bellows is compressed, thereby changing a height of fluid within a manometer fluidly coupled to the bellows. However, accuracy of the hypodermic manometer of the '887 patent may depend upon orientation of the manometer with respect to gravity, making it difficult to use with accuracy in practice. Moreover, a rupture or leak of the bellows poses the risk of mixing the manometer fluid with the fluid in contact with the occlusive cuff.

Pressure indicators including a bellows within a hollow housing made of a transparent material, such that an indicator mark on the bellows is visible through the housing, are known for use with pressure cuff devices. However, accuracy of such indicators may be sensitive to variations in the resilience of the bellows, which in turn is sensitive to variations in bellows geometric and material properties.

Accordingly, methods and apparatus are desired for indicating pressure in an inflatable cuff that are insensitive to geometric and material variations, and that are insensitive to the spatial orientation of the apparatus.

SUMMARY OF THE INVENTION

One aspect of the present invention advantageously provides a pressure indicating device including a housing defining a cylindrical bore therein, and a piston movably disposed within the cylindrical bore. The housing includes a first portion that is permeable to visible light, a first end member, and a second end member opposite the first end member. A first variable volume is defined by the cylindrical bore, the piston, and the first end member of the housing. A second variable volume is defined by the cylindrical bore, the piston, and the second end member of the housing, such that the second variable volume is sealed between the piston and the second end member of the housing. An inlet port is defined by the first end member of the housing and is in fluid communication with the first variable volume. A piston bypass channel is disposed outside the cylindrical bore and is in fluid communication with the inlet port. An outlet port is defined by the second end member of the housing, such that the outlet port is in fluid communication with the piston bypass channel.

Another aspect of the present invention advantageously provides an inflatable inflatable cuff, a tube fluidly coupled to the inflatable inflatable cuff, and a pressure indicating device fluidly coupled to the inflatable inflatable cuff through the tube. The pressure indicating device includes a housing defining a cylindrical bore therein, and a piston movably disposed within the cylindrical bore. The housing includes a first portion that is permeable to visible light, a first end member, and a second end member opposite the first end member. A first variable volume is defined by the cylindrical bore, the piston, and the first end member of the housing, and a second variable volume is defined by the cylindrical bore, the piston, and the second end member of the housing, such that the second variable volume is sealed between the piston and the second end member of the housing. An inlet port is defined by the first end member of the housing and is in fluid communication with the first variable volume. A piston bypass channel is disposed outside the cylindrical bore and is in fluid communication with the inlet port. An outlet port is defined by the second end member of the housing, such that the outlet port is in fluid communication with the piston bypass channel.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. Therefore, the claims shall be regarded as including such equivalent constructions insofar as they do not depart from the spirit and scope of the present invention.

DETAILED DESCRIPTION

Figure 1:
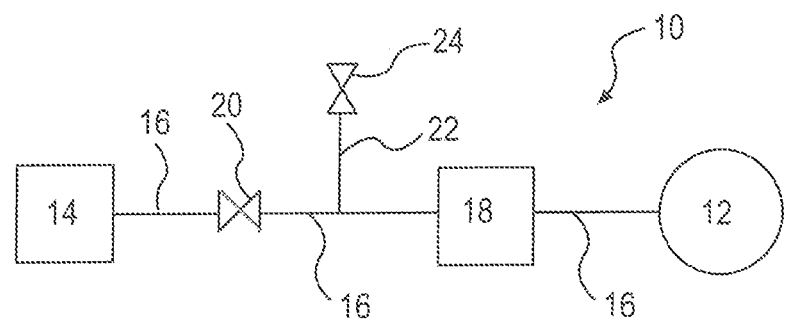
FIG. 1 presents a schematic view of a pressure cuff system according to an embodiment of the present invention.

The invention will now be described with reference to the drawing figures, in which like reference numerals refer to like parts throughout. An embodiment in accordance with the present invention provides a pressure indicator for detecting an inflation pressure applied to an inflatable cuff.

FIG. 1 presents a schematic view of a pressure cuff system 10 according to an embodiment of the present invention. The pressure cuff system 10 includes an inflatable cuff 12 in fluid communication with a pressurized fluid source 14 through a supply channel 16. The pressure cuff system 10 further includes a pressure indicator 18 in fluid communication with the supply channel 16, such that a flow of pressurizing fluid from the pressurized fluid source 14 flows through the pressure indicator 18 en route to the inflatable cuff 12. The pressurizing fluid may include any liquid fluid, such as water, or any gaseous fluid, such as air, for example.

The pressure cuff system 10 may include a first valve 20 disposed in the supply channel 16, and a second valve 24 branching off from the supply channel 16 and in fluid communication therewith. In one embodiment of the present invention, the first valve 20 is a check valve oriented such that the first valve 20 permits flow only in a direction from the pressurized fluid source 14 toward the inflatable cuff 12. In another embodiment of the present invention, the first valve 20 is a normally-closed, spring-loaded isolation valve that is configured to be opened by a syringe luer engaging the pressure cuff system 10 as the pressurized fluid source 14. In yet another embodiment of the present invention, the valve 24 is a manually operated bleed valve. In still yet another embodiment of the present invention, the valve 24 is a spring-loaded pressure relief valve that is configured to vent pressure from the inflatable cuff 12 at a threshold high pressure.

The pressurized fluid source 14 could include any pump, such as, for example, a syringe, an elastic bulb, a rotary pump, or a positive displacement pump; a plenum pressurized with a fluid; combinations thereof; or any other means for supplying a pressurized fluid known to persons with ordinary skill in the art. The inflatable cuff 12 could include an elastic membrane or other structure that expands upon pressurization known to persons with ordinary skill in the art. Examples of the inflatable cuff 12 include an endotracheal tube or a tracheostomy tube.

Figure 2:
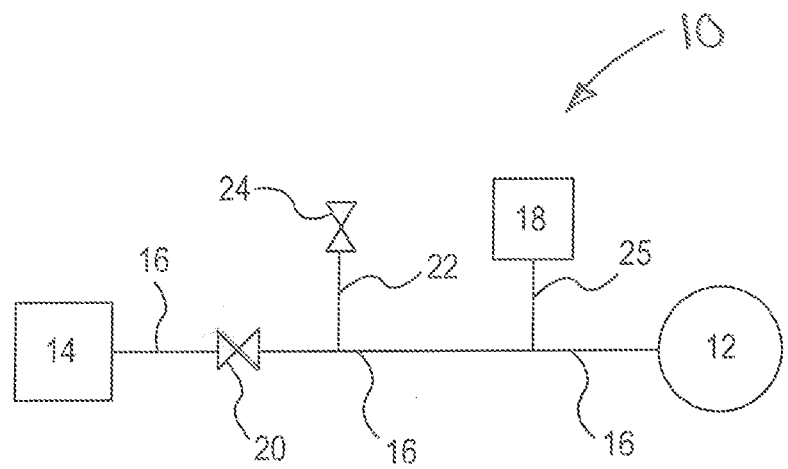
FIG. 2 presents a schematic view of a pressure cuff system according to another embodiment of the present invention.

FIG. 2 presents a schematic view of a pressure cuff system 10 according to an alternate embodiment of the present invention. In FIG. 2, the pressure indicator 18 is in fluid communication with the supply channel 16 through a branch channel 25. Here, the pressure indicator 18 has an inlet in fluid communication with the supply channel 16 but no outlet.

Figure 3:
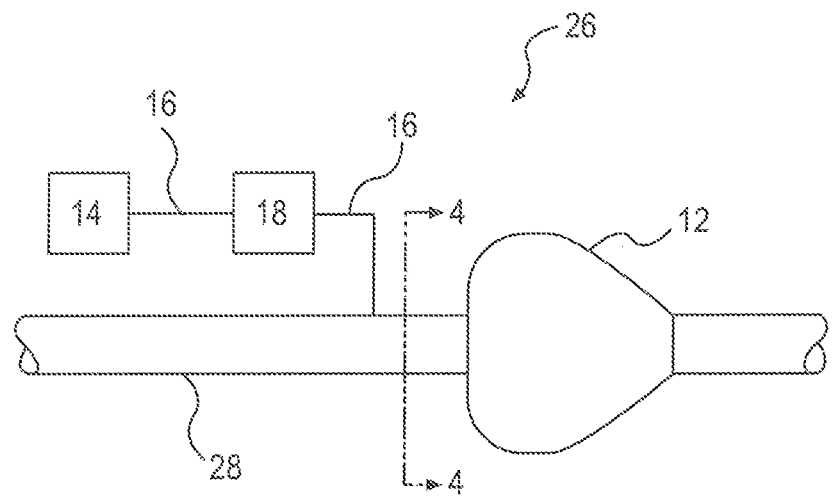
FIG. 3 presents a schematic view of an endotracheal tube system according an embodiment of the present invention.
Figure 4:
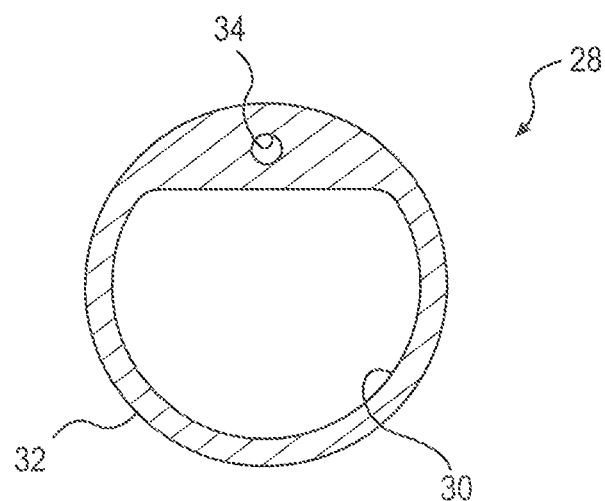
FIG. 4 shows a cross section of the endotracheal tube system illustrated in FIG. 3 along section 4--4.

Referring now to FIGS. 3 and 4, it will be appreciated that FIG. 3 presents a schematic view of an endotracheal tube system 26 according an embodiment of the present invention; and FIG. 4 shows a cross section of the endotracheal tube system 26 illustrated in FIG. 3 along section 4--4. The endotracheal tube system 26 includes an elongated tube 28, defining a main lumen 30 (see FIG. 4) therethrough. The inflatable cuff 12 is disposed around an outer periphery 32 of the elongated tube 28. In one embodiment, the inflatable cuff 12 defines an annular volume therein, which surrounds the elongated tube 28.

The elongated tube 28 may further define an inflation lumen 34 (see FIG. 4), which is fluidly coupled to a volume within the inflatable cuff 12. The supply channel 16 may be fluidly coupled to the inflation lumen 34, thereby effecting fluid communication between the inflatable cuff 12 and the pressurized fluid source 14.

Figure 5:
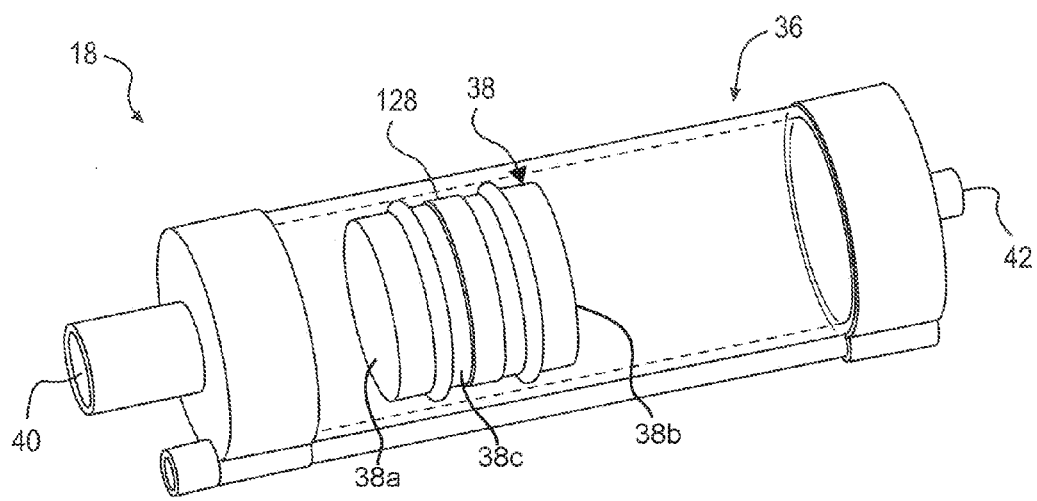
FIG. 5 presents a perspective view of a pressure indicator according to an embodiment of the present invention.

FIG. 5 presents a perspective view of a pressure indicator 18 according to an embodiment of the present invention. The pressure indicator 18 includes a housing 36 and a piston 38 movably disposed within the housing. The piston 38 includes a first wall 38a, a second wall 38b, and a body 38c extending between the first wall 38a and the second wall 38b. The housing 36 defines an inlet port 40 and may define an exit port 42. The pressure indicator 18 may be fluidly coupled to the supply channel 16 through both the inlet port 40 and the exit port 42 (see FIG. 1), or coupled to the supply channel 16 through only the inlet port 40 when there is no exit port 42 (see FIG. 2).

Figure 6:
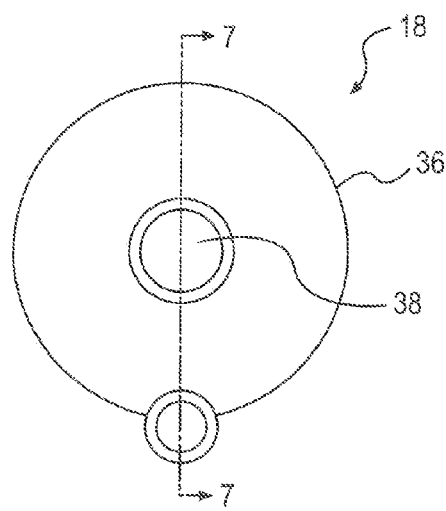
FIG. 6 shows a left-side view of the pressure indicator in FIG. 5.
Figure 7:
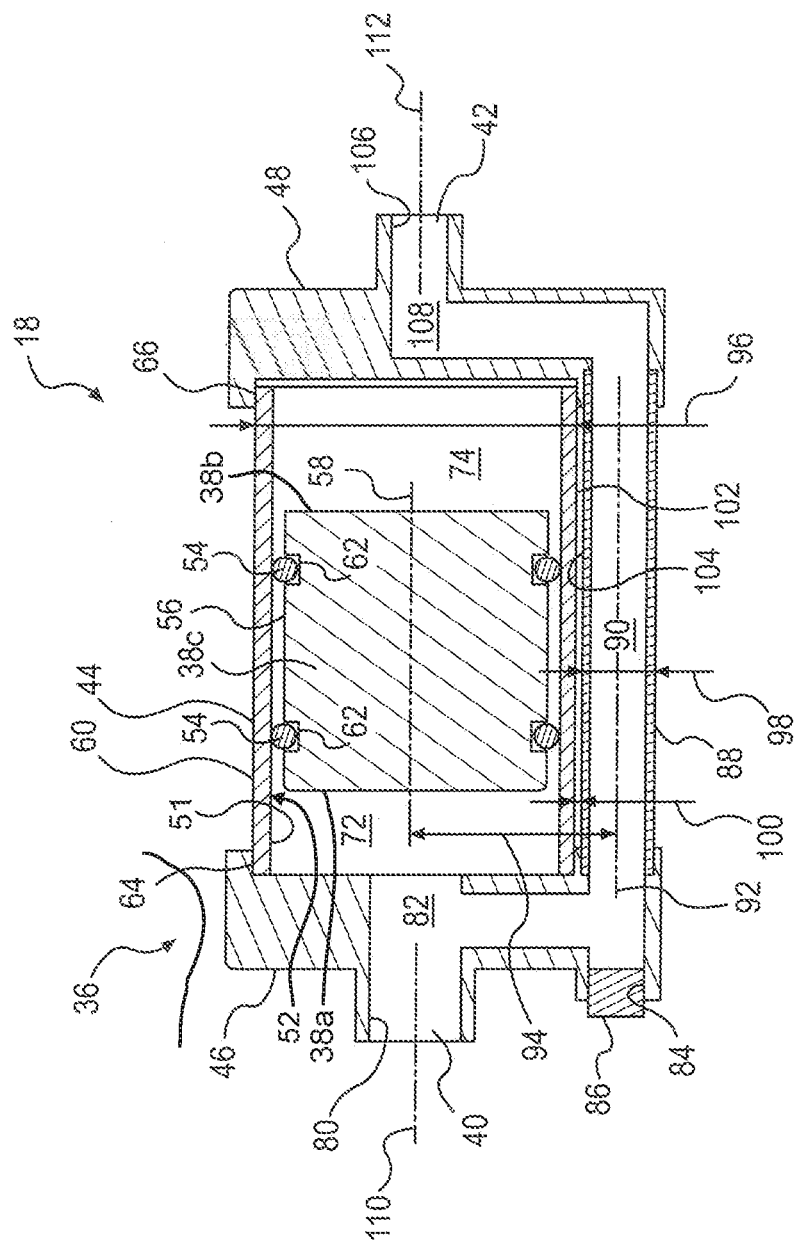
FIG. 7 shows a cross sectional view of the pressure indicator illustrated in FIG. 6 along section 7--7.

Referring now to FIGS. 6 and 7, it will be appreciated that FIG. 6 shows a leftside view of the pressure indicator 18 in FIG. 5; and that FIG. 7 shows a cross sectional view of the pressure indicator illustrated in FIG. 6 along section 7--7. The housing 36 includes a barrel 44 disposed between an inlet end member 46 and an exit end member 48. An internal surface 51 of the barrel 44 defines a bore 52 therein. In one embodiment of the present invention, the bore 52 has a generalized cylindrical shape and extends along an axis 58 of the bore 52. In another embodiment of the present invention, the bore 52 has a circular cylindrical shape. The external surface 60 of the barrel 44 may or may not have the same shape as the bore 52.

The piston 38 may engage the internal surface 51 defining the bore 52 of the barrel 44 through one or more seals 54 disposed about a peripheral surface 56 of the piston 38. In one embodiment of the present invention, the piston 38 includes only one seal 54. In another embodiment of the present invention the piston 38 includes at least two seals 54. However, it will be appreciated that the piston 38 may incorporate any number of seals 54.

The one or more seals 54 may have an o-ring structure. The o-ring structure could have a round cross section; a polygonal cross section, such as a square cross section; an elliptical cross section; a C-shaped cross section; a J-shaped cross section; a W-shaped cross section, or other o-ring cross section known to persons with ordinary skill in the art. Further, the one or more seals 54 may be disposed within one or more circumferential grooves 62 defined by the peripheral surface 56 of the piston 38.

An interface 64 between the barrel 44 and the inlet end member 46 forms a fluid-tight seal therebetween. Further, an interface 66 between the barrel 44 and the exit end member 48 may form a fluid-tight seal therebetween. The barrel 44 may be joined to the inlet end member 46 or the exit end member 48 by welding, adhesive bonding, threaded connection, or other joining methods known to persons with ordinary skill in the art.

Figure 9:
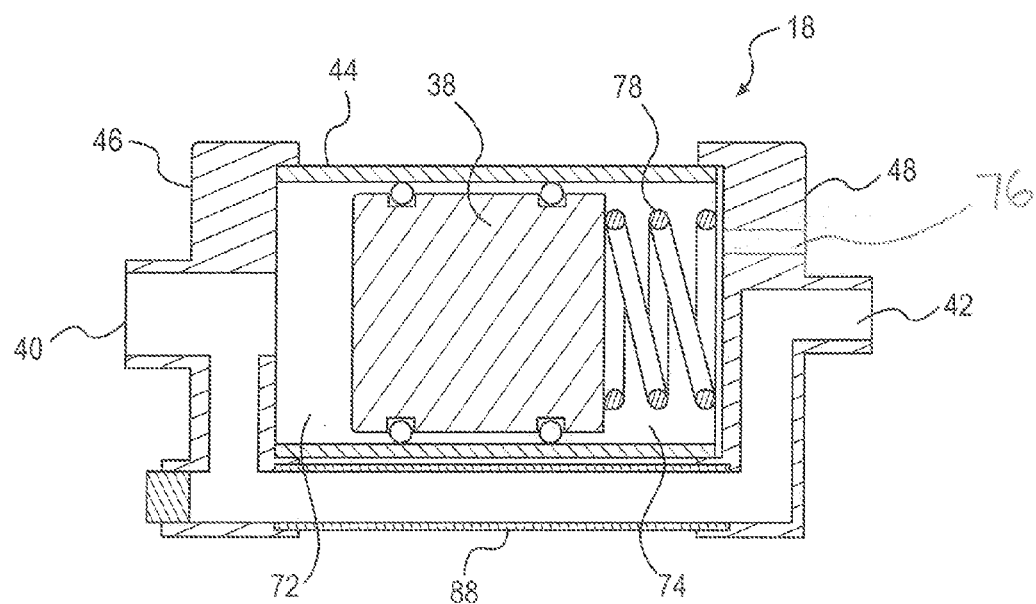
FIG. 9 shows a cross sectional view of another embodiment of the pressure indicator illustrated in FIG. 6 along section 7--7.

The internal surface 51, the inlet end member 46, and the piston 38 define a first variable volume 72. According to one aspect of the present disclosure, a part of the piston 38 that defines the first variable volume 72 includes a surface of the first wall 38a. Further, the internal surface 51, the exit end member 48, and the piston 38 define a second variable volume 74. According to one aspect of the present disclosure, a part of the piston 38 that defines the second variable volume 74 includes a surface of the second wall 38b. In one embodiment of the present invention, the second volume 74 is completely sealed between the internal surface 51, the exit end member 48, and the piston 38. Optionally, in the alternative, the exit end member 48 defines a bleed channel 76, which is in fluid communication with the second volume 74 and an ambient environment of the pressure indicator 18; and a resilient member 78 (see FIG. 9) biases the piston 38 toward the inlet end member 46. The resilient member 78 could be a compression spring disposed within the second volume 74 (as shown in FIG. 9), or a tension spring disposed within the first volume 72 (not shown), for example.

An internal portion 80 of the inlet end member 46 defines a first fluid channel 82 therethrough. The first fluid channel 82 is in fluid communication with the inlet port 40 and the first volume 72. The internal portion 80 of the inlet end member 46 may further define a relief port 84 containing a pressure relief device 86. The pressure relief device could include a frangible element such as a burst disk, a resilient stopper press fit into the relief port 84, a pressure actuated valve, or other pressure relief device known to persons of ordinary skill in the art. When the pressure relief device 86 is activated by an excess of pressure within the first fluid channel 82, the first fluid channel is in fluid communication with the ambient environment of the pressure indicator 18 via the relief port 84.

The housing 36 further includes a piston bypass tube 88 defining a bypass channel 90 therein. In one embodiment of the present invention, the piston bypass tube 88 is a straight tube having an axis 92 that is substantially parallel to the axis 58 of the bore 52. In another embodiment of the present invention, a distance 94 between the axis 92 of the piston bypass tube 88 and the axis 58 of the bore 52 is greater than the sum of an outer diameter 96 of the barrel 44 and an outer diameter 98 of the piston bypass tube 88 divided by two (distance 94>[diameter 96+diameter 98]/2).

An outer surface 102 of the barrel 44 and an outer surface 104 of the piston bypass tube 88 may form a gap 100 therebetween. In one embodiment, the gap 100 is not greater than the outer diameter 98 of the piston bypass tube 88. Alternatively, there may be no gap between the outer surface 104 of the piston bypass tube 88 and the outer surface 102 of the barrel 44.

An internal surface 106 of the exit end member 48 may further define a second fluid channel 108 therein. The second fluid channel 108 is in fluid communication with the bypass channel 90 and the exit port 42, such that the exit port 42 may be in fluid communication with an inflatable cuff 12 through the supply channel 16 (see FIGS. 1 and 3). In one embodiment of the present invention, the second fluid channel 108 is not in fluid communication with the second volume 74.

An axis 110 of the first fluid channel 82 may be substantially coaxial with an axis 112 of the second fluid channel 108. Further the axis 110 of the first fluid channel 82, the axis 112 of the second fluid channel 108, and the axis 58 of the bore 52 may all be substantially coaxial with one another.

It will be appreciated that the parallel alignment and close proximity of the piston bypass tube 88 relative to the barrel 44 results in an advantageously compact, in-line, configuration for the pressure indicator 18. It will also be appreciated that substantially coaxial alignment of the axis 58 of the bore 52 with either of the axis 110 of the first fluid channel 82, or the axis 112 of the second fluid channel 108 may further promote an advantageously compact arrangement that beneficially accommodates in-line installation as part of a fluid channel.

Figure 8:
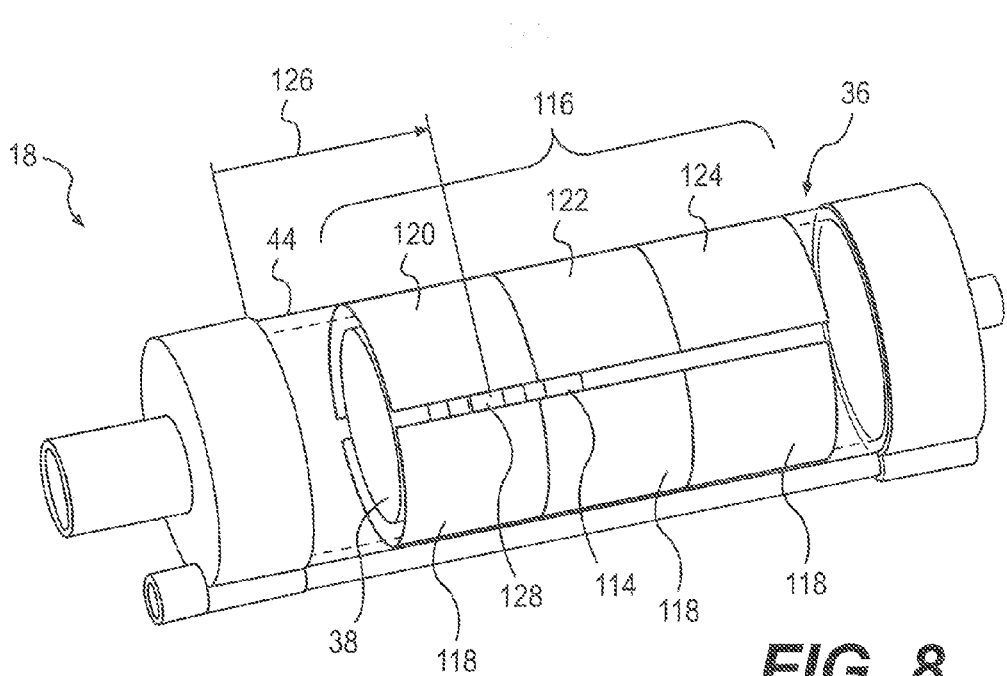
FIG. 8 presents a perspective view of further aspects of a pressure indicator according to one or more embodiments of the present invention.

FIG. 8 presents a perspective view of further aspects of a pressure indicator according to one or more embodiments of the present invention. As illustrated in FIG. 8, at least a portion 114 of the barrel 44 is permeable to visible light, such that the piston 38 is visible through the portion 114. The portion 114 may be transparent or merely translucent. The barrel 44 may be made from materials that are permeable to visible light such as, for example, glass, clear polymers, combinations thereof, or other structural materials permeable to visible light that are known to persons of ordinary skill in the art.

Pressure indicia 116 may be disposed on the barrel 44. In one embodiment, the pressure indicia 116 are disposed adjacent to the portion 114 of the barrel 44 that is permeable to visible light. In another embodiment, the pressure indicia 116 are themselves permeable to visible light, such that the piston 38 is visible through both the barrel 44 and the pressure indicia 116. The pressure indicia 116 may include a plurality of discrete zones 118 disposed along a axial direction of the barrel 44. In one embodiment of the present invention, the plurality of discrete zones 118 includes a first zone 120, a second zone 122, and a third zone 124, all arranged sequentially along the axial direction of the barrel 44. In another embodiment of the present invention, the first zone 120 has a yellow color, the second zone 122 has a green color, and the third zone 124 has a red color.

When a pressure inside the first volume 72 is atmospheric pressure, the piston location within the bore 52 may be biased toward the inlet end member 46. The piston may be biased toward the inlet end member by a balance of pressure between the first volume 72 and the second volume 74; the resilient member 78 acting on the piston 38; a charge of gas stored within the second volume 74 having a pressure greater than atmospheric pressure; or combinations thereof, for example.

As pressure is applied from the pressurized fluid source 14 to the inlet port 40 of the pressure indicator 18 through the supply channel 16, the pressure imparts a force tending to displace the piston 38 in a direction along the axis 58 of the bore 52 from the inlet end member 46 toward the exit end member 48. Displacement of the piston in a direction toward the exit end member 48 performs work on gas disposed within the second volume 74, the resilient member 78, or combinations thereof, thereby imparting a reaction force against the pressure force imparted onto the piston by the pressure in the first volume. Thus, an axial location 126 of the piston 38 within the bore 52 is functionally related to the pressure within the first volume.

It will be appreciated that the functional relationship between the axial location 126 of the piston within the bore 52 and a pressure within the first volume 72 does not depend on structural parameters or material properties of a complex bellows element. Accordingly, apparatus and methods for indicating pressure according to embodiments of the present invention promote measurement accuracy over conventional approaches by eliminating sources of manufacturing variation that can affect calibration.

In one embodiment, the piston 38 has a hollow structure and is made from a light weight material such as a polymer, for example. In turn, the piston 38 can be made having a very low weight, such that accuracy of the pressure indicator 18 is not sensitive to a spatial orientation of the pressure indicator 18 with respect to gravity.

The piston 38 may include an indicator mark 128, which defines a reference position on the piston 38 for identifying the axial location 126 of the piston 38 within the pressure indicator 18. Accordingly, a location of the indicator mark 128 relative to the pressure indicia 116 may provide an indication of pressure within the first volume 72 of the pressure indicator 18.

In one embodiment of the present invention, the first zone 120 of the pressure indicia 116 corresponds to a range of pressures that are below a first target pressure, the third zone 124 corresponds to a range of pressures that are above a second target pressure, and the second zone 122 corresponds to a range of acceptable pressures between the first target pressure and the second target pressure. Accordingly, the indicator mark 128 disposed within the first zone 120 may indicate that a measured pressure is low, the indicator mark 128 disposed within the second zone 122 may indicate that a measured pressure is acceptable, and the indicator mark disposed with the third zone 124 may indicate that the measured pressure is high.

Although the pressure indicator 18 is useful to indicate a fluid pressure within a pressure cuff system 10, the pressure indicator 18 can also be used to measure fluid pressure in other systems that could benefit from either quantitative or qualitative indication of a fluid pressure.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A pressure indicating device, comprising:
a housing including:
an internal surface defining a cylindrical bore within the housing,
a first portion that is permeable to visible light,
a first end member, and
a second end member positioned opposite to the first end member along a longitudinal axis of the cylindrical bore;
a piston movably disposed within the cylindrical bore,
a first variable volume defined by the internal surface, the piston, and the first end member of the housing;
a second variable volume defined by the internal surface, the piston, and the second end member of the housing, such that the second variable volume is sealed between the piston and the second end member of the housing;
an inlet port defined by the first end member of the housing and in fluid communication with the first variable volume;
a piston bypass channel disposed outside the cylindrical bore and in fluid communication with the inlet port; and
an outlet port defined by the second end member of the housing, the outlet port in fluid communication with the piston bypass channel,
wherein the piston is configured to move and be located along the longitudinal axis of the cylindrical bore according to only a fluid pressure in the first variable volume and a fluid pressure in the second variable volume.

2. The pressure indicating device of claim 1, wherein a longitudinal axis of the piston bypass channel is substantially parallel to the longitudinal axis of the cylindrical bore.

3. The pressure indicating device of claim 1, wherein an axis of the inlet port is substantially coaxial with the longitudinal axis of the cylindrical bore.

4. The pressure indicating device of claim 1, wherein an axis of the outlet port is substantially coaxial with the longitudinal axis of the cylindrical bore.

5. The pressure indicating device of claim 1, further comprising at least one seal disposed between the piston and the internal surface of the housing.

6. The pressure indicating device of claim 5, wherein the at least one seal consists of a plurality of seals.

7. The pressure indicating device of claim 1, further comprising pressure indicia disposed on the housing.

8. The pressure indicating device of claim 7, further comprising an indicator mark on the piston, such that a location of the indicator mark with respect to the pressure indicia indicates a pressure in the first variable volume.

9. The pressure indicating device of claim 7, wherein the pressure indicia demarcates three pressure magnitude regions, the three pressure magnitude regions disposed consecutively along a direction of the longitudinal axis of the cylindrical bore of the housing.

10. The pressure indicating device of claim 7,
wherein the pressure indicia are disposed on the first portion of the housing that is permeable to visible light, and
wherein the pressure indicia are permeable to visible light, such that the piston is visible through the pressure indicia and the first portion of the housing.

11. The pressure indicating device of claim 1,
wherein the first end member defines a relief port positioned downstream of the inlet port and upstream of piston bypass channel, and
wherein the relief port is in fluid communication with the inlet port and the piston bypass channel and configured to receive a pressure relief device.

12. The pressure indicating device of claim 1,
wherein a peripheral surface of the piston defines a first circumferential groove and a second circumferential groove,
wherein a seal is positioned in each of the first circumferential groove and the second circumferential groove to provide an engagement between the internal surface of the housing and the peripheral surface of the piston.

13. The pressure indicating device of claim 12, further comprising:
pressure indicia disposed on the housing; and
an indicator mark positioned on the peripheral surface of the piston between the first circumferential groove and the second circumferential groove along the longitudinal axis of the cylindrical bore,
wherein a location of the indicator mark with respect to the pressure indicia indicates a pressure in the first variable volume.

14. The pressure indicating device of claim 1,
wherein the piston includes a first wall, a second wall, and a body extending between the first wall and the second wall,
wherein a part of the piston that defines the first variable volume includes a surface of the first wall, and wherein a part of the piston that defines the second variable volume includes a surface of the second wall.

15. The pressure indicating device of claim 1,
wherein the internal surface of the housing is engaged with a peripheral surface of the piston and
wherein the piston is not connected with either the first end member or the second end member.

16. An inflatable cuff apparatus, comprising:
an inflatable cuff;
a tube fluidly coupled to the inflatable cuff; and
a pressure indicating device fluidly coupled to the inflatable cuff through the tube, the pressure indicating device including:
    a housing including:
        an internal surface defining a cylindrical bore within the housing,
        a first portion that is permeable to visible light,
        a first end member, and
        a second end member positioned opposite to the first end member along a longitudinal axis of the cylindrical bore,
    a piston movably disposed within the cylindrical bore,
    a first variable volume defined by the internal surface, the piston, and the first end member of the housing,
    a second variable volume defined by the internal surface, the piston, and the second end member of the housing, such that the second variable volume is sealed between the piston and the second end member of the housing,
    an inlet port defined by the first end member of the housing and in fluid communication with the first variable volume,
    a piston bypass channel disposed outside the cylindrical bore and in fluid communication with the inlet port, and
    an outlet port defined by the second end member of the housing, the outlet port in fluid communication with the piston bypass channel,
    wherein the piston is configured to move and be located along the longitudinal axis of the cylindrical bore according to only a fluid pressure in the first variable volume and a fluid pressure in the second variable volume.

17. The inflatable cuff apparatus of claim 16, wherein a longitudinal axis of the piston bypass channel is substantially parallel to the longitudinal axis of the cylindrical bore.

18. The pressure indicating device of claim 16,
wherein the internal surface of the housing is engaged with a peripheral surface of the piston, and
wherein the piston is not connected with either the first end member or the second end member.

* * * * *